US00PP12603P2

(12) United States Plant Patent
Vijverberg

(10) Patent No.: US PP12,603 P2
(45) Date of Patent: May 7, 2002

(54) DRACAENA PLANT NAMED 'GOLDEN COAST'

(75) Inventor: Piet Vijverberg, Honselersdijk (NL)

(73) Assignee: Kwekerji Piet Kijverberg, Honselersdijk (NL)

( * ) Notice: Subject to any disclaimer, the term of this patent is extended or adjusted under 35 U.S.C. 154(b) by 0 days.

(21) Appl. No.: 09/455,446

(22) Filed: Dec. 6, 1999

(51) Int. Cl.[7] ..... A01H 5/00
(52) U.S. Cl. ..... Plt./383
(58) Field of Search ..... Plt./383

(56) References Cited

PUBLICATIONS

GTITM UPOVROM Citation for 'Golden Coast' as per NL PBR DCN0003; Nov. 25, 1993.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Dracaena plant named 'Golden Coast', characterized by its unique golden and dark green-colored variegated foliage with dark green at leaf center surrounded by golden margin; upright and thick leaves; short leaf sheaths; and tolerance to low temperatures.

2 Drawing Sheets

BACKGROUND OF THE INVENTION

The present invention relates to a new and distinct cultivar of Dracaena plant, botanically known as *Dracaena fragrans,* and hereinafter referred to by the cultivar name 'Golden Coast'.

The new Dracaena is a naturally-occurring mutation of the *Dracaena fragrans* cultivar 'Steudneri' (not patented) with solid green leaves. The new Dracaena was discovered and selected by the Inventor in October, 1987, as an individual plant within a population of plants of the cultivar 'Steudneri' grown in a cultivated area in Naaldwijk, The Netherlands. The new Dracaena was selected on the basis of its unique golden leaf margins.

Asexual reproduction of the new cultivar by vegetative cuttings taken at Naaldwijk, The Netherlands, since 1988 has shown that the unique features of this new Dracaena are stable and reproduced true to type in successive generations.

SUMMARY OF THE INVENTION

Plants of the cultivar 'Golden Coast' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Golden Coast'. These characteristics in combination distinguish 'Golden Coast' as a new and distinct cultivar:

1. Unique golden and dark green-colored variegated foliage; dark green at leaf center surrounded by golden margin.

2. Upright and thick leaves.

3. Short leaf sheaths.

4. Tolerant to low temperatures.

In addition to leaf color, plants of the new Dracaena differ from plants of the parent cultivar 'Steudneri' in the following characteristics:

1. Plants of the new Dracaena have thicker leaves than plants of the cultivar 'Steudneri'.

2. Plants of the new Dracaena have shorter leaf sheaths than plants of the cultivar 'Steudneri'.

3. Leaves of plants of the new Dracaena are more upright than leaves of plants of the cultivar 'Steudneri'.

BRIEF DESCRIPTION OF THE PHOTOGRAPHS

The accompanying colored photographs illustrate the overall appearance of the new cultivar, showing the colors as true as it is reasonably possible to obtain in colored reproduction of this type. Colors in the photographs may differ slightly from the color values cited in the detailed botanical description which accurately describe the actual colors.

The photograph at the top of the first sheet comprises a side perspective view of a typical plant of the new Dracaena grown in a field planting.

The photograph at the bottom of the first sheet comprises a close-up view of a typical plant of the new Dracaena grown in a field planting.

The photograph on the second sheet comprises a close-up view of the foliage of the new Dracaena.

DETAILED BOTANICAL DESCRIPTION

In the following description, color references are made to The Royal Horticultural Society Colour Chart except where general terms of ordinary dictionary significance are used.

Plants used for the description were grown for about 16 weeks in a glass-covered greenhouse with day and night temperatures of about 21 and 20° C., respectively in Naadwijk, The Netherlands.

Botanical classification: *Dracaena fragrans* cultivar 'Golden Coast'.

Parentage: Naturally-occurring mutation of the *Dracaena fragrans* cultivar 'Steudneri' (not patented).

Propagation:

*Type cutting.*—Vegetative cuttings.

*Time to initiate and develop roots.*—About 14 days at 21° C.

*Root description.*—Thick, fibrous.

Plant description:

*Form.*—Upright, inverted triangle, symmetrical. Suitable for 11 to 30-cm containers. About 16 weeks are required to produce finished plants in Naaldwijk, The Netherlands.

*Vigor.*—Vigorous, rapid growth rate.

*Plant height* (*from soil level to top of plant plane*).—About 15 cm.

*Stem length.*—About 15 cm.

*Spreading area of plant.*—About 20 cm.

*Stem strength.*—Strong.

*Stem diameter.*—About 3 to 7 cm.

*Internode length.*—About 1 to 4 cm.

*Foliage description.*—Leaves simple, generally symmetrical and long persisting; sessile. Length: About 10 to 50 cm. Width: About 4 to 7 cm. Aspect: Somewhat upright. Shape: Linear to narrowly elliptic. Apex: Acute. Base: Truncate. Margin: Entire. Texture: Smooth, glabrous. Color: Typically dark green-colored centers with golden-colored margins; actual width of margin may be variable. Upper surface, young and mature leaves: Center, dark green, 138A; margin, golden, 9A. Lower surface, young and mature leaves: 144A. Venation, upper and lower surfaces: 138A. Leaf sheath length: About 4 cm. Leaf sheath color: 144A.

Inflorescence description: Inflorescences have not been observed on plants of the new Dracaena.

Disease resistance: Resistance to diseases common to Dracaena has not been observed to date.

Low temperature tolerance: Plants of the new Dracaena are tolerant to temperatures about 10° C.

It is claimed:

1. A new and distinct cultivar of Dracaena plant named 'Golden Coast', as illustrated and described.

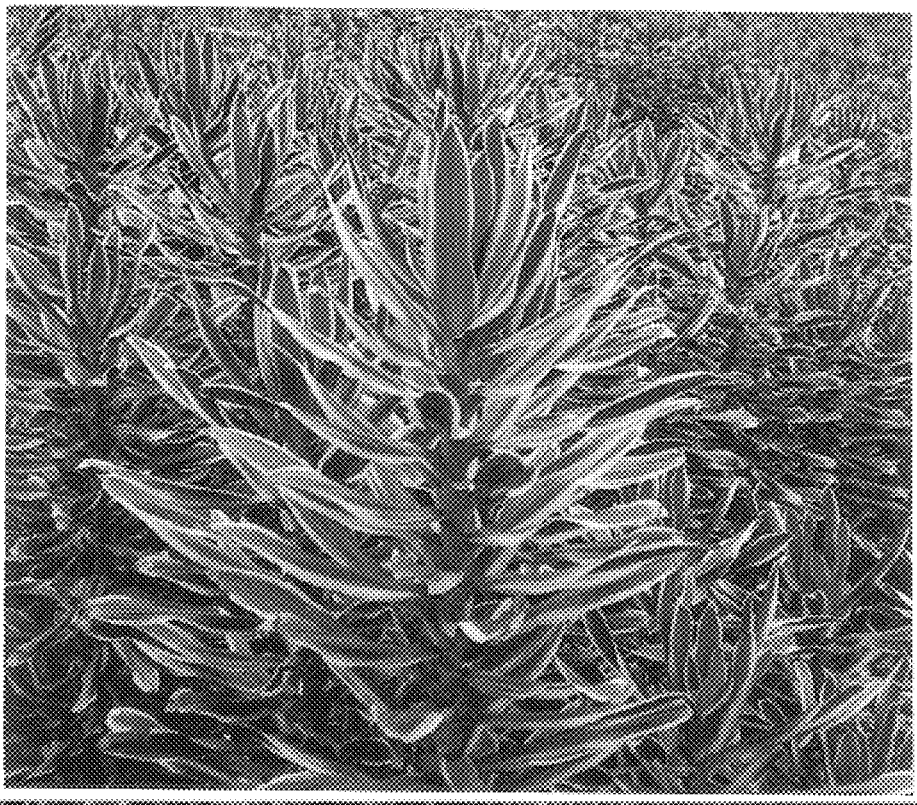
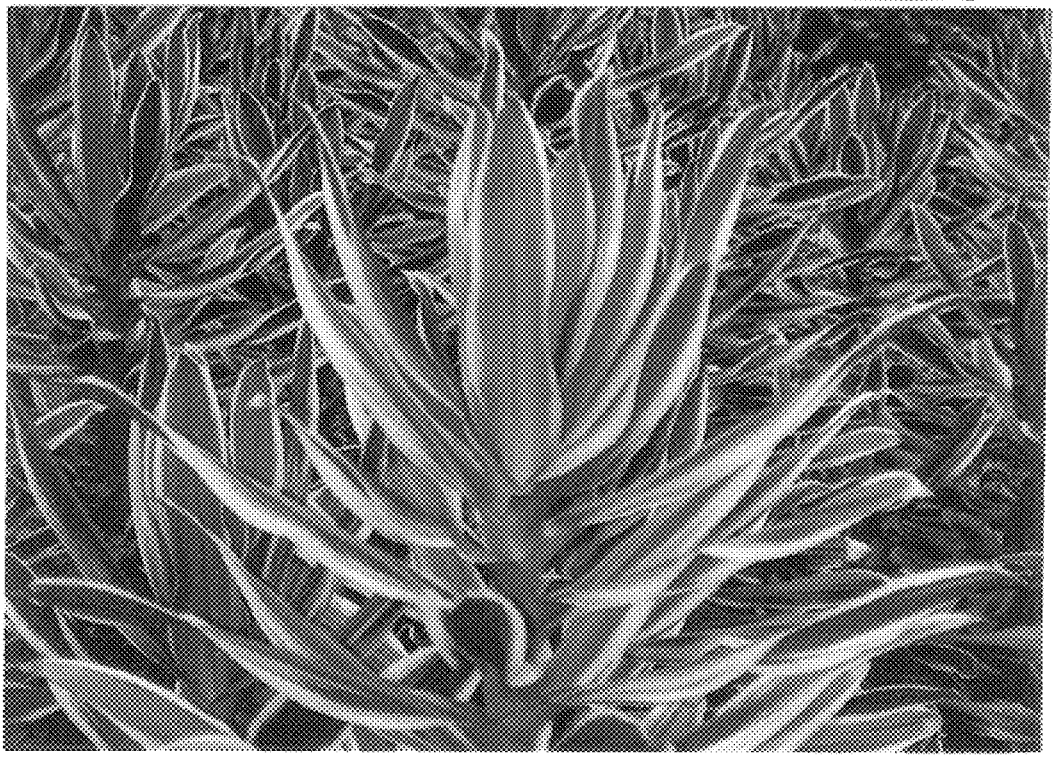

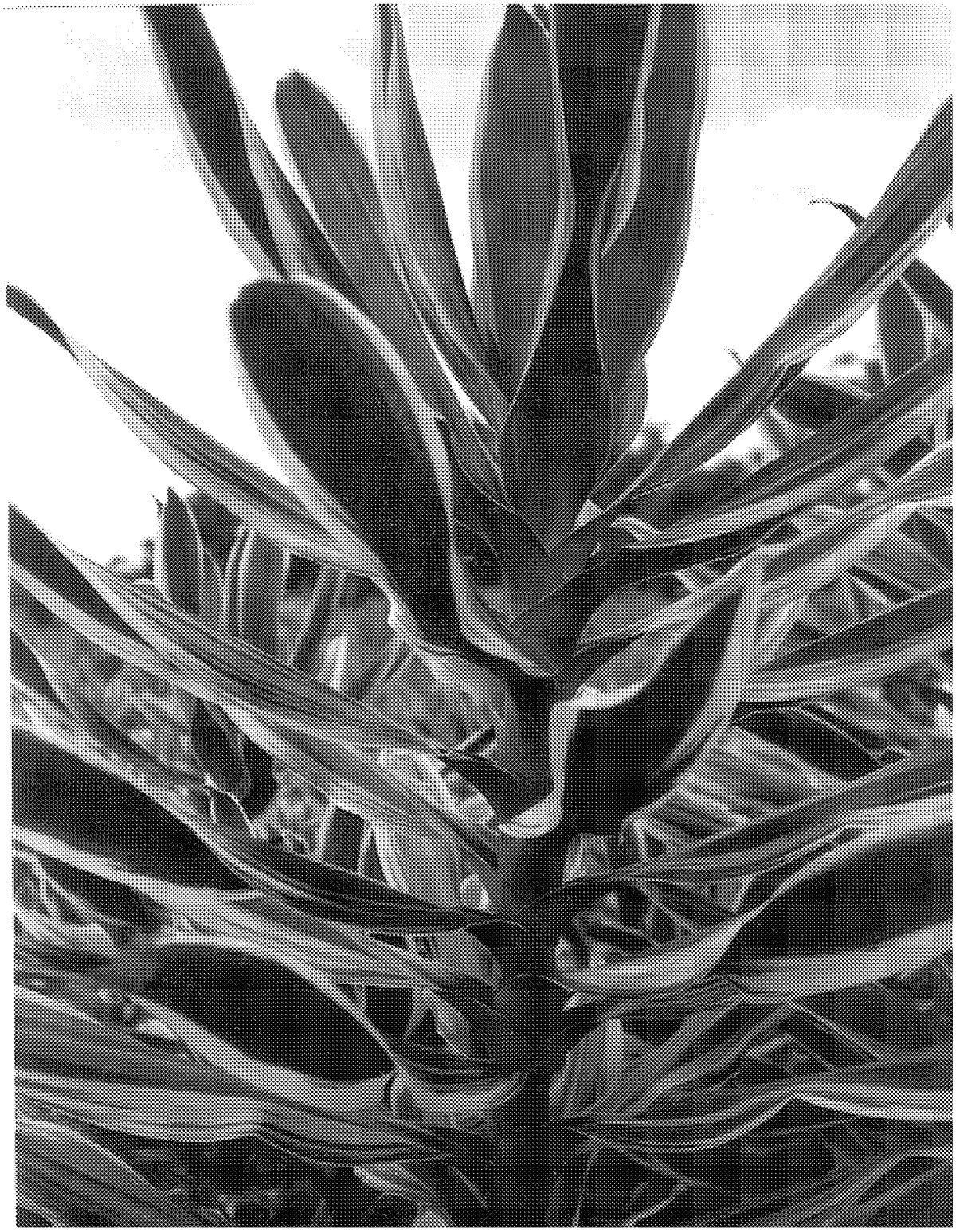

* * * * *